United States Patent [19]

Chan

[11] 4,427,697
[45] Jan. 24, 1984

[54] 1,2-DIPHENYLETHANE DERIVATIVES

[75] Inventor: Rosalind P. K. Chan, London, England

[73] Assignee: Biorex Laboratories Limited, England

[21] Appl. No.: 321,931

[22] Filed: Nov. 16, 1981

[30] Foreign Application Priority Data

Nov. 18, 1980 [GB] United Kingdom ............. 8036921

[51] Int. Cl.³ ............ C07C 39/16; C07C 49/813; C07C 69/21; A61K 31/055; A61K 31/05; A61K 31/12; A61K 31/22
[52] U.S. Cl. ............................ 424/311; 560/138; 568/331; 568/729; 424/331; 424/341; 424/346; 424/347
[58] Field of Search ............... 560/138; 568/331, 334, 568/726, 729; 424/311, 331, 341, 346, 347

[56] References Cited

U.S. PATENT DOCUMENTS 3,960,931 6/1976 Chan ................................. 560/138
4,051,263 9/1977 Turner et al. ..................... 568/729

FOREIGN PATENT DOCUMENTS 523320 7/1940 United Kingdom ............ 568/729

Primary Examiner—Natalie Trousof
Assistant Examiner—L. Hendriksen
Attorney, Agent, or Firm—Wenderoth, Lind & Ponack

[57] ABSTRACT

The present invention provides 1,2-diphenylethane derivatives of the general formula:

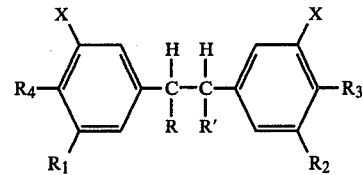

wherein X is a hydrogen or halogen atom, R and R', which may be the same or different, are alkyl radicals optionally substituted by halogen atoms, $R_1$ and $R_2$, which may be the same or different, are acyl radicals, hydroxyl groups or acylated hydroxyl groups and $R_3$ and $R_4$, which may be the same or different, are hydroxyl groups or acylated or alkylated hydroxyl groups.

The present invention also provides processes for the preparation of these compounds and pharmaceutical compositions containing them.

8 Claims, No Drawings

1,2-DIPHENYLETHANE DERIVATIVES

BACKGROUND OF THE INVENTION

Although compounds are known which possess antio-estrogenic properties, there is a need for new and improved compounds with this property and it is, therefore, an object of the present invention to provide new compounds with anti-oestrogenic properties.

SUMMARY OF THE INVENTION

Thus, according to the present invention, there are provided 1,2-diphenylethane derivatives of the general formula:

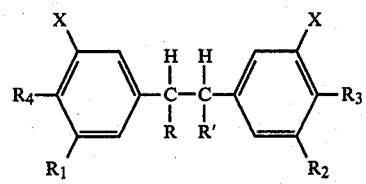

wherein X is a hydrogen or halogen atom, R and R', which may be the same or different, are alkyl radicals optionally substituted by halogen atoms, $R_1$ and $R_2$, which may be the same or different, are acyl radicals, hydroxyl groups or acylated hydroxyl groups and $R_3$ and $R_4$, which may be the same or different, are hydroxyl groups or acylated or alkylated hydroxyl groups.

DETAILED DESCRIPTION OF THE INVENTION

The halogen atoms X are preferably fluorine atoms. When R and R' are alkyl radicals, they preferably contain up to 6 carbon atoms and when R and R' are halogen-substituted alkyl radicals, the halogen substituents are preferably fluorine atoms, the $\beta,\beta,\beta$-trifluoroethyl radical being especially preferred. When $R_1$ and $R_2$ are acyl radicals, they preferably contain up to 4 carbon atoms, the acetyl radical (—CO.CH$_3$) being especially preferred, and when $R_1$ and $R_2$ are acylated or alkylated hydroxyl groups they again preferably contain up to 4 carbon atoms, the methoxy and acetoxy radicals (O.-CO.CH$_3$) being especially preferred.

The compounds (I) according to the present invention may be prepared from a compound of the general formula:

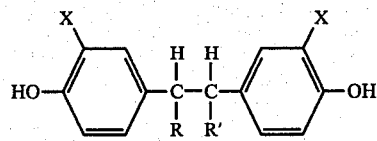

in which X, R and R' have the same meanings as above, by first acylating to give the corresponding 4,4'-diacyloxy compound which, by heating with aluminum chloride, undergoes rearrangement to give a compound (I) in which $R_1$ and $R_2$ are both acyloxy radicals, whereafter, if desired, this compound is oxidised under basic conditions to give the corresponding 4,4',5,5'-tetrahydroxy compound which, if desired, is then acylated to give the corresponding 4,4',5,5'-tetraaceyloxy compound.

Alternatively, the compounds (I) according to the present invention can be prepared from a compound of the general formula:

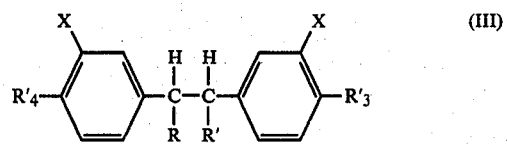

in which R, R' and X have the same meanings as above and R'$_3$ and R'$_4$, which may be the same or different, are alkylated hydroxyl groups, by reaction with an acyl halide in the presence of titanium tetrachloride to give a compound of general formula (I), in which $R_3$ and $R_4$, which may be the same or different, are alkylated hydroxyl groups and $R_1$ and $R_2$, which may be the same or different, are acyloxy radicals, whereafter, if desired, this compound is dealkylated, for example with hydrobromic acid in glacial acetic acid, to give the corresponding compound of general formula (I), in which $R_3$ and $R_4$ are both hydroxyl groups, and, if desired, this compound is oxidised under basic conditions to give the corresponding 4,4',5,5'-tetrahydroxy compound which, if desired, is then acylated to give the corresponding 4,4',5,5'-tetraacyloxy compound.

The starting materials of general formulae (II) and (III) are known compounds, some of which are described in U.S. Pat. Nos. 3,960,931 and 4,051,263. However, these known compounds possess oestrogenic properties, in contradistinction to the compounds of the present invention, which possess anti-oestrogenic properties.

The following Examples are given for the purpose of illustrating the present invention:

EXAMPLE 1

4.5 g. erythro-3,3'-Difluoro-4,4'-dihydroxy-α-ethyl-α'-methylbibenzyl in 30 ml. pyridine and 10 ml. acetic anhydride were left to stand for 24 hours at ambient temperature, whereafter the reaction mixture was worked up to give a crude product, recrystallisation of which from chloroform-diethyl ether (1:4 v/v) gave 5.5 g. erythro-3,3'-difluoro-4,4'-diacetoxy-α-ethyl-α'-methylbibenzyl; m.p. 118°–120° C.

5 g. of this diacetoxy were ground with 10 g. aluminium chloride and the mixture was heated at 150° C. for 30 minutes. After cooling, the mass was added portionwise to ice, stirred and extracted with chloroform. The chloroform solution was washed with water, dried with anhydrous sodium sulphate and concentrated to half its volume. An equal volume of diethyl ether was added thereto and the solution was treated with charcoal and filtered. The filtrate was evaporated and the residue obtained was crystallised from chloroform-diethyl ether (1:1 v/v) to give 2.6 g. erythro-3,3'-diacetyl-4,4'-dihydroxy-5,5'-difluoro-α-ethyl-α'-methylbibenzyl; m.p. 194°–196° C.

EXAMPLE 2

0.9 g. erythro-3,3'-Diacetyl-4,4'-dihydroxy-5,5'-difluoro-α-ethyl-α'-methylbibenzyl was suspended in a mixture of 10 ml. dioxan and 6 ml. 1 N aqueous sodium hydroxide solution. The solution was cooled to 10° C. and 0.8 ml. 30% hydrogen peroxide added dropwise thereto. The reaction mixture was stirred at 20° C. for 1.5 hours and then poured into a mixture of dilute hydrochloric acid and ice. The product was extracted with peroxide-free diethyl ether, the extract was evaporated and the residue was crystallised from benzene to give a yellow solid. This was treated in 5 ml. ethanol with 2 mg. sodium borohydride, followed by acidification with hydrochloric acid, rapid extraction with diethyl ether, evaporation of the extract and immediate crystallisation from benzene to give 350 mg. of pure erythro-4,4′,5,5′-tetrahydroxy-3,3′-difluoro-α-ethyl-α′-methylbibenzyl; m.p. 143°–145° C.

EXAMPLE 3

1. g. erythro-3,3′-Difluoro-4,4′,5,5′-tetrahydroxy-α-ethyl-α′-methylbibenzyl in a mixture of 10 ml. pyridine and 5 ml. acetic anhydride was left to stand at 20° C. for 20 hours and at 60° to 80° C. for 1 hour. The reaction mixture was then poured into a mixture of dilute hydrochloric acid and ice, stirred for several hours and filtered. The filtrate was evaporated and the residue was taken up in chloroform and the chloroform solution was washed with dilute hydrochloric acid and water, dried over anhydrous sodium sulphate and the solvent removed. The gummy residue was taken up with benzene and the benzene solution filtered through a neutral alumina. The benzene was removed from the filtrate and the residue was crystallised from diethyl ether to give 1 g. pure erythro-3,3′-difluoro-4,4′,5,5′-tetraacetoxy-α-ethyl-α′-methylbibenzyl; m.p. 160°–162° C.

EXAMPLE 4

5 ml. Titanium tetrachloride were added dropwise at 0° C., while stirring, to a solution of 7.5 g. erythro-4,4′-dimethoxy-α-methyl-α′-(2,2,2-trifluoroethyl)-bibenzyl in 8 ml. acetyl chloride. The reaction mixture was further stirred for 4 hours, during which time the temperature was allowed to increase to 20° C., whereafter it was decomposed with ice and water, diethyl ether being added in order to facilitate decomposition. The product obtained was filtered off, washed with water, taken up in chloroform and treated with charcoal, filtered and the filtrate evaporated. The evaporation residue was crystallised from chloroform and diethyl ether (1:1 v/v) to give 8 g. erythro-3,3′-diacetyl-4,4′-dimethoxy-α-methyl-α′-(2,2,2-trifluoroethyl)-bibenzyl; m.p. 185.5°–187° C.

8 g. erythro-3,3′-Diacetyl-4,4′-dimethoxy-α-methyl-α′-(2,2,2-trifluoromethyl)-bibenzyl in 100 ml glacial acetic acid and 50 ml. hydrobromic acid were heated under gentle reflux for 3 hours, whereafter thin layer chromatography indicated that the reaction was complete. The reaction mixture was cooled and poured into ice and water, followed by extraction with chloroform. The chloroform solution was washed with water, dried, treated with charcoal, filtered and the filtrate evaporated to dryness. The evaporation residue was crystallised from diethyl ether to give erythro-3,3′-diacetyl-4,4′-dihydroxy-α-methyl-α′-(2,2,2-trifluoroethyl)-bibenzyl; m.p. 124°–125° C.

EXAMPLE 5

A solution of 3.5 g. erythro-3,3′-diacetyl-4,4′-dihydroxy-α-methyl-α′-(2,2,2-trifluoroethyl)-bibenzyl in 30 ml. dioxan and 20 ml. 1 N aqueous sodium hydroxide solution was cooled to 0° to 5° C. and 2.5 ml. 30% hydrogen peroxide added thereto dropwise, while stirring. The reaction mixture was then stirred at 0° to 5° C. for 30 minutes and at 20° C. for 1 hour. Ice and water were added to the reaction mixture, followed by acidification with 2 N hydrochloric acid, and then by extraction with peroxide-free diethyl ether. The ethereal solution was washed with water until neutral and then shaken with 2 mg. sodium borohydride. After having again been washed with water, it was dried with anhydrous sodium sulphate and evaporated to dryness. The evaporation residue was crystallised from dichloromethane to give 2.5 g. erythro-3,3′,4,4′-tetrahydroxy-α-methyl-α′-(2,2,2-trifluoroethyl)-bibenzyl; m.p. 147.5°–149° C.

The present invention also includes within its scope anti-oestrogenic pharmaceutical compositions containing one or more of the new compounds. These pharmaceutical compositions can be administered orally or parenterally in admixture with a solid or liquid pharmaceutical diluent or carrier.

Solid compositions for oral administration include compressed tablets, pills, dispersible powders and granules. In such solid compositions, at least one active compound according to the present invention is admixed with at least one inert diluent, such as tribasic calcium phosphate ($Ca_3(PO_4)_2$), starch, lactose, gelatine, acacia, sucrose, stearic acid, talc, alginic acid or sodium alginate. The compositions may also comprise, as is normal practice, additional substances other than inert diluents, for example, lubricating agents, such as magnesium stearate, as well as sweetening or flavouring agents.

The percentage of active ingredient in the compositions of the present invention may be varied, it being necessary that it should constitute a proportion such that a suitable dosage for the desired therapeutic effect shall be obtained. In general, the preparations of the present invention should be administered in an effective dose from about 0.00001 mg. to 1 mg. of active substance per kg. of body weight per day.

The following Example illustrates a pharmaceutical composition according to the present invention:

EXAMPLE 6

Ingredients for the preparation of 100,000 tablets, each containing 20 μg. of active material:

| | |
|---|---|
| erythro-3,3′-difluoro-4,4′,5,5′-tetrahydroxy-α-ethyl-α′-methylbibenzyl | 2.00 g. |
| lactose | 3900.00 g. |
| starch | 998.00 g. |
| magnesium stearate | 100.00 g. |

The lactose was first milled to a fine powder and sieved into the bowl of a planetary or trough mixer. The bibenzyl derivative was dissolved in 100 ml. ethanol and mixed with the lactose, mixing being continued for 30 minutes. The starch was sieved and sufficient pure water added thereto to give a 10% by weight starch paste. After subtracting the amount paste was introduced into the mixing vessel and mixing continued for 15 minutes. Granulation was then carried out with the calculated quantity of starch paste at ambient temperature and mixing continued for a further 15 minutes.

The granulate obtained was sieved through a 16 mesh screen, laid out in a thin layer and dried for 12 hours with forced ventilation at a temperature of 35°–40° C. The dried granulate was then sieved through a 20 mesh screen and returned to the planetary or trough mixer. The magnesium stearate was then sieved through a 60 mesh screen, added to the granulate and mixing continued for 30 minutes. The granulate was then compressed into 50 mg. tablets, each of which contained 20 μg. of the bibenzyl derivative.

I claim:

1. 1,2-Diphenylethane derivatives of the general formula:

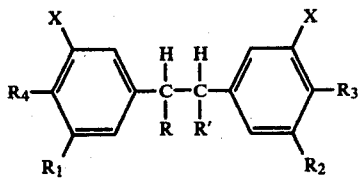

wherein X is a hydrogen or fluorine atom, R is a methyl or ethyl radical, R' is a methyl, ethyl or 2,2,2-trifluoroethyl radical, $R_1$ and $R_2$ which are the same or different, are hydroxyl groups or acetyl radicals and $R_3$ and $R_4$, which are the same or different, are hydroxyl, methoxy or acetoxy, with the proviso that, when X is a hydrogen R' is 2,2,2-trifluoroethyl.

2. erythro-3,3'-Diacetyl-4,4'-dihydroxy-5,5'-difluoro-α-ethyl-α'-methylbibenzyl.

3. erythro-4,4',5,5'-tetrahydroxy-3,3'-difluoro-α-ethyl-α'-methylbibenzyl.

4. erythro-4,4',5,5'-Tetraacetoxy-3,3'-difluoro-α-ethyl-α'-methylbibenzyl.

5. erythro-3,3'-Diacetyl-4,4'-dimethoxy-α-methyl-α'-(2,2,2-trifluoroethyl)-bibenzyl.

6. erythro-3,3'-Diacetyl-4,4'-dihydroxy-α-methyl-α'-(2,2,2-trifluoroethyl)-bibenzyl.

7. erythro-3,3',4,4'-Tetrahydroxy-α-methyl-α'-(2,2,2-trifluoroethyl)-bibenzyl.

8. The pharmaceutical composition for administration to a human requiring anti-oestrogenic therapy, containing at least one compound according to claim 1 in an anti-oestrogenically effective amount, in admixture with a solid or liquid pharmaceutical diluent or carrier.

* * * * *